(12) United States Patent
Hechel et al.

(10) Patent No.: US 6,270,471 B1
(45) Date of Patent: *Aug. 7, 2001

(54) ULTRASONIC PROBE WITH ISOLATED OUTER CANNULA

(75) Inventors: Dennis L. Hechel, Gurnee, IL (US); William Edelman, Sharon, MA (US); John C. Brumbach, Chicago; Joseph F. Brumbach, Niles, both of IL (US)

(73) Assignee: Misonix Incorporated, Farmingdale, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/996,778

(22) Filed: Dec. 23, 1997

(51) Int. Cl.[7] .............................. A61B 17/20; A61B 17/32; A61M 1/00
(52) U.S. Cl. ........................ 604/22; 606/169; 604/35
(58) Field of Search .................... 604/22, 35, 73; 606/169–171

(56) References Cited

U.S. PATENT DOCUMENTS

| | | |
|---|---|---|
| 2,227,727 | 1/1941 | Leggiadro . |
| 3,805,787 * | 4/1974 | Banko .......................... 604/22 |
| 3,896,811 | 7/1975 | Storz . |
| 3,990,452 | 11/1976 | Murry et al. . |
| 4,428,748 * | 1/1984 | Peymon et al. ............... 604/22 |
| 4,493,694 | 1/1985 | Wuchinich . |
| 4,681,106 | 7/1987 | Kensey et al. . |
| 4,728,319 | 3/1988 | Masch . |
| 4,775,365 | 10/1988 | Swartz . |
| 4,804,364 * | 2/1989 | Dieras et al. ............... 604/22 |
| 4,815,462 | 3/1989 | Clark . |
| 4,886,491 | 12/1989 | Parisi et al. . |
| 4,932,935 | 6/1990 | Swartz . |
| 5,037,432 | 8/1991 | Molinari . |
| 5,112,302 | 5/1992 | Cucin . |
| 5,123,903 | 6/1992 | Quaid et al. . |
| 5,190,518 | 3/1993 | Takasu . |
| 5,211,625 * | 5/1993 | Sakurai et al. ............ 604/22 |
| 5,236,414 | 8/1993 | Takasu . |
| 5,242,386 | 9/1993 | Holzer . |
| 5,244,458 | 9/1993 | Takasu . |
| 5,254,082 * | 10/1993 | Takase ........................ 604/22 |
| 5,282,820 | 2/1994 | Goodstein . |
| 5,348,535 | 9/1994 | Cucin . |
| 5,419,761 | 5/1995 | Narayanan et al. . |
| 5,514,086 | 5/1996 | Parisi et al. . |
| 5,562,609 | 10/1996 | Brumbach . |
| 5,562,610 | 10/1996 | Brumbach . |
| 5,569,178 | 10/1996 | Henley . |
| 5,643,198 | 7/1997 | Cucin . |
| 5,772,627 * | 6/1998 | Acosta et al. ............. 604/22 |
| 5,817,050 | 10/1998 | Klein . |

* cited by examiner

Primary Examiner—Sharon Kennedy
Assistant Examiner—Michael J. Hayes
(74) Attorney, Agent, or Firm—Welsh & Katz, Ltd.

(57) ABSTRACT

An electronic surgical probe including an axially elongated member adapted to receive ultrasonic vibrations from an ultrasonic motor or transducer and having a circular cross-section, has a coaxially positioned cannula or sheath surrounding the elongated member, the cannula or sheath defining an aperture adjacent the distal end portion of the elongated member, wherein fluid adjacent the distal end portion of the elongated member is activated or cavitated by ultrasonic vibrations from the distal end of the elongated member and passing through the aperture of the cannula acts upon tissue and/or other matter.

3 Claims, 3 Drawing Sheets

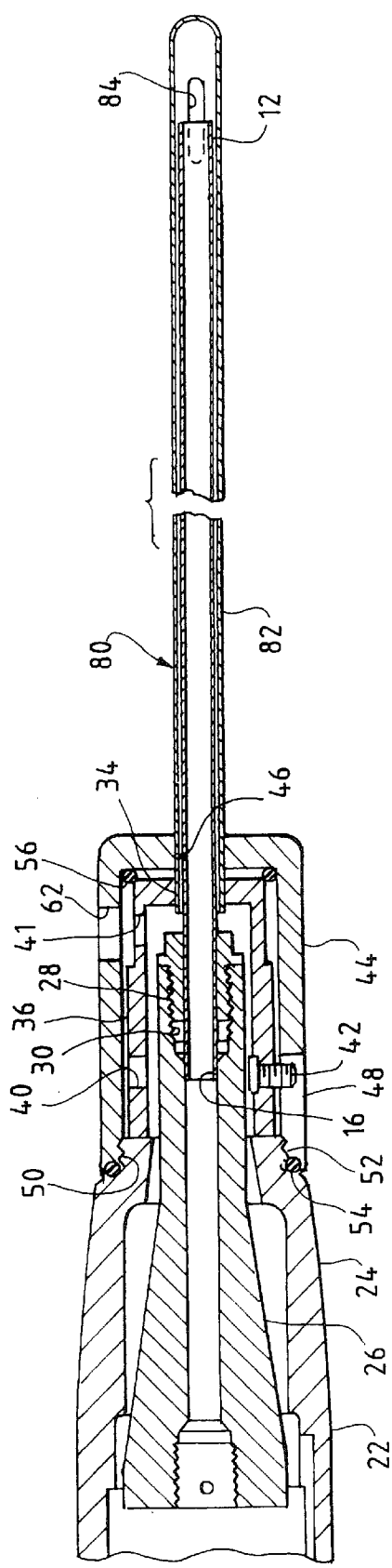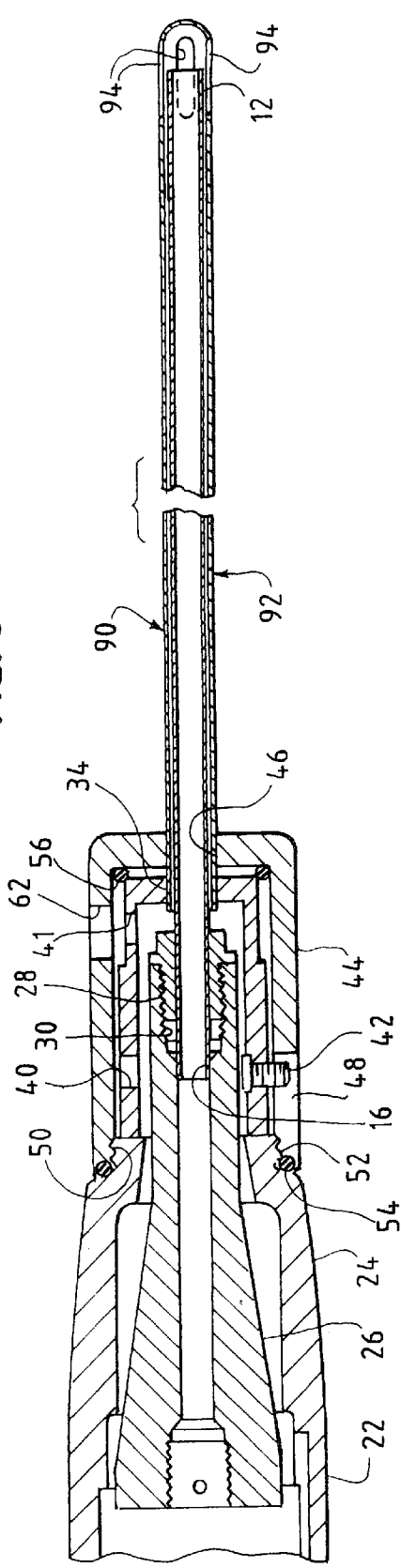

ULTRASONIC PROBE WITH ISOLATED OUTER CANNULA

BACKGROUND OF THE INVENTION

1. Field of the Invention

The present invention relates to ultrasonic surgical probes or ultrasonic cutting devices for use in the removal of tissue and/or matter from a living body, and more particularly, to an improved ultrasonic probe which is capable of removing tissue through activation or cavitation of a fluid by ultrasonic vibration, and in which the ultrasonically activated member contains minimal features which may cause weakened portions.

2. Description of Related Art

Probes or scalpels for the fragmentation and removal of materials, tissue and fluids from living beings are known to the art. For example, U.S. Pat. No. 2,227,727, issued Jan. 7, 1941 to Vincent Leggiardro, discloses an apparatus for fragmenting naturally formed stones, such as kidney stones, and the like, utilizing a high speed reciprocating rod which may have a blunt end, a sharp or chisel point, a cutting blade, or combination thereof, such as a cutting blade having a blunt end.

While the apparatus disclosed in U.S. Pat. No. 2,227,727 involved a two part housing, with the sonic transducer in one part and the reciprocating rod in another part, in later apparatus the transducer and probe were connected together to form a unitary instrument. In U.S. Pat. No. 3,896,811, issued Jul. 29, 1975 to Karl Storz, the transducer and rod-like are coupled and both enveloped by a jacket providing an air gap and preventing the sides of the probe from contacting the body except at its end. An improvement in such instruments is disclosed in U.S. Pat. No. 3,990,452, issued Nov. 9, 1976 to Edward J. Murry and Joseph F. Brumbach, which also reviews a number of articles relating to the development of ultrasonics in medicine and notes the incorporation of irrigation and aspiration with ultrasonics.

A particular arrangement in an ultrasonically vibrated surgical tool using an irrigation fluid and an anti-coagulant is disclosed in U.S. Pat. No. 4,493,694, issued Jan. 15, 1985, to David G. Wuchinich, utilizes a hollow tool having a suction passage and at least one pre-aspirating orifice in the wall of the tool, and a plastic sleeve concentrically spaced about the tool for admitting fluid from a supply into the space between the tool and passing substantially all of the fluid through the pre-aspirating orifice.

In the application of ultrasonics to liposuction, instruments of varying configurations recently have been proposed. In U.S. Pat. No. 5,236,414, issued Aug. 17, 1993 to Katsuya Takasu, a tubular body defining a suction passage has an opening in its front lower end, and an outer tube having a corresponding opening, by means of which fat tissue is crushed and/or emulsified due to the vibration of the front end of the tubular body and is then aspirated. In U.S. Pat. No. 5,514,086, issued May 7, 1996, to Parisi et al., an ultrasonically vibrated hollow probe has a port in its surface for aspiration and a tip substantially formed of plastic.

In the previously known probes, particularly for the fragmentation or emulsification and aspiration of fat tissue, the ultrasonically activated member or tool had one or more ports or openings, which have been found to be points of stress which limited the amount of ultrasonic power which could be applied thereto, or limited the amount of travel or excursion of the distal end of the probe. If the power limit of the probe were exceeded, the probe was in danger of cracking at the points of stress, particularly at the ports or suction openings. Thus, there is a need for an improved ultrasonic surgical probe configuration which reduces the stress on the probe at higher ultrasonic power levels and at higher excursion of the distal end of the probe.

SUMMARY OF THE INVENTION

Therefore, it is one object of the present invention to provide an improved ultrasonic surgical probe for use in the removal of matter from a living body.

It is another object of the present invention to provide an improved ultrasonic surgical probe capable of removing tissue and/or matter of hard or soft nature through activation or cavitation of a fluid by ultrasonic vibration and aspiration of fluid and tissue.

It is still another object of the present invention to provide an improved ultrasonic surgical probe capable of emulsifying and removing tissue and other matter through activation or cavitation of a fluid by ultrasonic vibration and aspiration of fluid and tissue.

Still another object of the present invention is to provide a surgical probe which can be used to remove soft tissue from a living body by causing a fluid to emulsify the soft tissue through activation or cavitation of the fluid and aspiration of fluids and emulsified tissue.

Another object of this invention is to provide an ultrasonic surgical probe which can control the amount of tissue removed from a living body through emulsification of tissue by activation or cavitation of a fluid by ultrasonic vibration by controlling the size of an aperture in a cannula or sheath of the probe.

These and other objects and advantages of the present invention will be apparent from the following description considered in conjunction with the accompanying drawings.

In accordance with the present invention an improved ultrasonic surgical probe for removing material from a living body is provided having an axially elongated member having a circular cross-section, a proximal end portion adapted to receive ultrasonic vibrations and a distal end portion; and a coaxially positioned cannula or sheath surrounding the elongated member, isolated from the transmission of ultrasonic vibrations to the member and having an opening adjacent the distal end portion of the member.

The elongated member of the probe is desirably mounted to a handpiece manipulable by a surgeon in which or through which ultrasonic vibrations are imparted or transmitted to the proximal end portion of the member, and causing the distal end portion of the member to have successive axial excursions capable of activating or cavitating a fluid adjacent its distal end portion. The elongated member can be solid or can be hollow, and preferably is of a metal or alloy or other material capable of transmitting ultrasonic vibrations therethrough while maintaining its structural integrity upon receiving and transmitting such vibrations. Preferably the member is formed of titanium or an alloy of titanium.

The cannula or sheath which surrounds the elongated member can also be mounted to the handpiece, but in a manner which isolates the cannula from the transmission of ultrasonic vibrations to the elongated member. The mounting of the cannula to the handpiece in an isolated manner can be the same type of mounting shown for the sleeve in U.S. Pat. No. 5,562,609, issued Oct. 8, 1996 to Joseph F. Brumbach. The cannula or sheath in the present invention is termed a cannula as it is that part of the probe which is intended to be inserted into the opening or cavity of the body of a patient from or through which matter such as stones, tumors and tissue is to be removed. More particularly, and as one embodiment, the opening can be an incision made in a selected portion of the skin of a patient through which tissue, such as soft or fatty tissue, underlying the skin is to be removed, as in liposuction.

The cannula is desirably formed of a metal or an alloy of two or more metals, such as stainless steel, or other material, preferably extends beyond the distal end of the elongated member, and has at least one aperture at or adjacent its distal end portion. In the operation of the probe of the present invention, fluid surrounding the distal end portion of the elongated member, which is initially confined by the cannula, is believed to be activated by the ultrasonic vibrations and/or the successive excusions of the distal end portion of the member, and through the opening in the cannula adjacent the distal end of the member, causes the fragmentation and/or emulsification of tissue of the body of the patient in the area of the distal end portion of the cannula. The fragmented or emulsified tissue and fluid can then be aspirated from the site of the probe.

In one embodiment of the present invention, the distal end of the cannula, extending beyond the distal end of the elongated member, may be blunt, and, in a further embodiment, the cannula can be open-ended, the open end of the cannula constituting the opening in the distal end portion of the cannula. In either embodiment, the fluid can be supplied to the distal end portion of the elongated member through the annular space between the elongated member and the cannula, for example, in the same manner that irrigation fluid is supplied in the annular space between the needle and the sleeve in U.S. Pat. No. 5,562,609. The fluid in the area of the distal end portion of the elongated member is activated by the ultrasonic vibrations from or excusions of the distal end portion of the member, and acts on tissue as the fluid exits the opening at the distal end portion of the cannula. In a still further embodiment, the elongated member can be hollow and constitute a suction or aspiration passage in the same manner as in the needle in U.S. Pat. No. 5,562,609, and provide the aspiration passage for the removal of tissue and fluid through the opening in the distal end of the cannula.

In a second embodiment, the cannula can have a closed distal end which can be blunt or rounded, and has at least one opening through the side of the cannula in its distal end portion. In this embodiment, the amount of tissue to be removed from the body per unit of time can be controlled by the dimensions of the opening or openings. Fluid can be supplied to the distal end portion of the elongated member, and acted upon by the ultrasonic vibrations and/or the excusions of the member, in the same manner as in the previously described embodiments. The fluid and tissue can be aspirated in the same manner in a further embodiment wherein the elongated member is hollow, is provided with suction and constitutes a suction passage of the probe.

In another embodiment of the present invention, the distal end portion of the cannula is rounded, and is partially cut away to expose part of the distal end and part of the side of the cannula, thereby also exposing the distal end portion of the elongated member.

As a consequence of the present invention as described above, the elongated member which receives and transmits ultrasonic vibrations is mainly free of any apertures, caps or other potential points of stress in its side surface, thus minimizing points where structural failure can occur upon being subject to repeated or higher ultrasonic frequency or amplitude than the elongated member can withstand if higher stress points were present. Additionally, the outer element, i.e., the cannula, which is intended to be inserted into the incision or body cavity, is also relatively free of stress as it is isolated from the transmission of ultrasonic vibrations to the elongated member. The improved probe of the present invention permits the elongated member to have excursions up to several times the excursion distance of elongated members with apertures in its side surface or caps on its end, and the probe provides effective cavitation and emulsification of such soft tissue as fat tissue. Additionally, since the elongated member is not connected to the cannula at the distal end it is free to move without the added stress of pulling the cannula along with it.

BRIEF DESCRIPTION OF THE DRAWINGS

FIG. 5 is a sectional view similar to FIG. 4, of another embodiment of the probe of the present invention; and FIG. 6 is a sectional side view similar to FIG. 4, of still another embodiment of the probe of the present invention.

DESCRIPTION OF THE PREFERRED EMBODIMENTS

Figure 1:
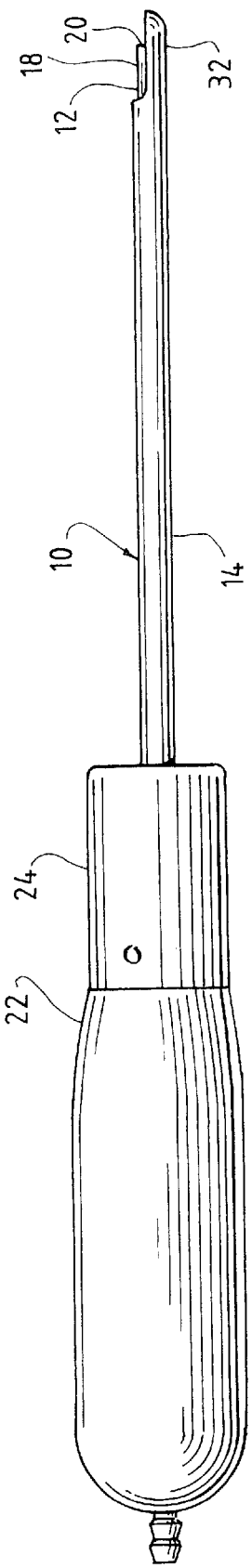
FIG. 1 is a side view of one embodiment of the probe of the present invention mounted to a handpiece.
Figure 2:
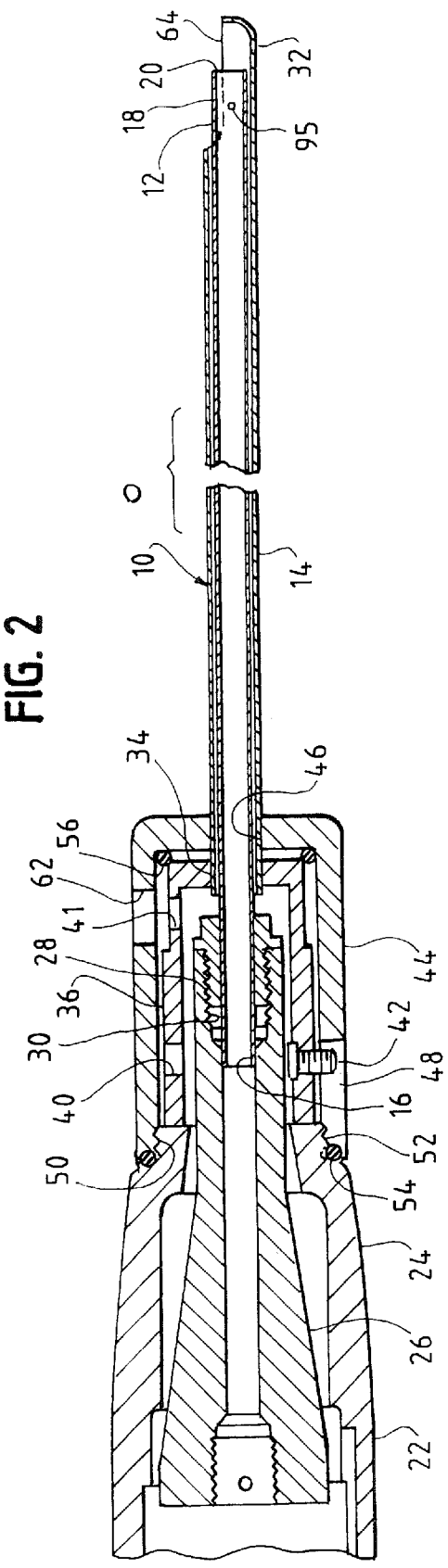
FIG. 2 is an enlarged sectional side view of the embodiment of the probe shown in FIG. 1 and a portion of a handpiece to which it is mounted.

In one preferred embodiment of the present invention, which is schematically illustrated in FIGS. 1 and 2, the probe is generally referenced by numeral 10. Probe 10 comprises an elongated member 12, which can be hollow as shown or can be solid (not shown), and a coaxially positioned cannula 14 which surrounds member 12. Member 12 has a proximal end portion 16 and a distal end portion 18 which terminates in a transverse distal end 20, i.e., end 20 is perpendicular to the elongation along the axis of member 12.

Elongated member 12 is mounted to a handpiece 22, which preferably has a housing 24 of non-conducting material, such as a polymer. Handpiece 22 encloses an ultrasonic motor or transducer (not shown) which may be of a type known to the art which is coupled to a member, such as horn 26, capable of transmitting ultrasonic vibrations generated by the ultrasonic motor or transducer. In the embodiment shown in the drawings, proximal end portion 16 of member 12 is mounted to horn 26, for example, by portion 16 having external threads 28 and horn 26 having internal threads 30, and threadingly engaging the former with the latter.

Cannula 14 is also mounted to handpiece 22, but in a manner which isolates cannula 14 from the ultrasonic vibrations being transmitted from horn 26 to member 12 and cannula 14. In particular, cannula 14 has a distal end portion 32 and a proximal end portion 34, which is affixed, for example, by brazing to and partially through a cup-shaped member 36, which is preferably formed of a metal or an alloy, such as stainless steel. For the sake of clarity, member 36 will be referred to herein as "cup 36". Cup 36 also has two diametrically opposed apertures 38 and 40 in its cylindrical surface spaced from its distal end. Cup 36 further has three apertures 41 equidistantly spaced about the surface of cup 36 to enable the passage of fluid therethrough as will be hereinafter described. Aperture 38 is dimensioned to hold a pin (not shown) or a screw 42, or a similar fastener, such as a rivet (not shown) for a purpose to be hereafter described. Where screw 42 is used as the fastener-like member, aperture 38 is tapped to enable screw 42 to be advanced through and extend outwardly of the wall of cup 36.

Cannula 14 and attached cup 36 are secured to handpiece 22 by means of a cup-shaped front piece 44, which has an aperture 46 in its otherwise closed distal end which is axially aligned and adapted to receive member 12. Front piece 44, desirably is formed of a non-conductive material, preferably of a non-flexible polymer. Front piece 44 also has a slot, i.e., a keyway 48, extending from its open, proximal end toward its distal end. Keyway 48 is adapted to receive screw 42 to prevent relative rotation of cup 36 and cannula 14 with respect to front piece 44 about their common axis. Front piece 42 has internal threads 50 adjacent its open, proximal end adapted to engage external threads 52 on the distal end of housing 24 of handpiece 22.

Figure 3:
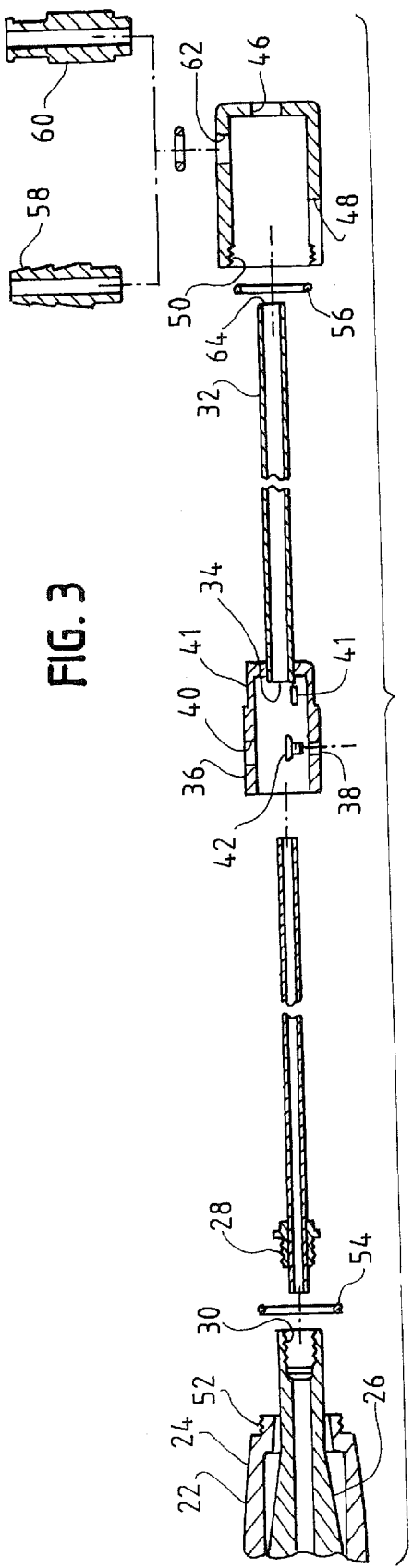
FIG. 3 is an exploded sectional side view of another embodiment of the present invention with alternate fittings for the supply of fluid through the annular space between the elongated member and the cannula.

As best shown in FIG. 3, probe 10 can be assembled by first threadingly securing member 12 to horn 26 by means of threads 28 of the former engaging threads 30 of the latter. A wrench (not shown), such as a torque wrench, can be used to tightly secure member 12 to horn 26. Screw 42 is placed in aperture 38 and advanced through the wall of cup 36 by inserting a screw driver (not shown) through aperture 40 and rotating screw 42. A relatively compressible sealing member, such as O-ring 54, of neoprene or similar substance, is placed about the threaded end of housing 24. Cup 36 and attached cannula 14 is then placed over elongated member 12 with member 12 passing through the hollow bore of cannula 14 until proximal end 34 of cannula 14 abuts the distal end of housing 24. An annular spacer, such as washer 56, is placed within front piece 44 so that it abuts against its inside circular corner at its distal end. Washer 56 preferably is formed, such as by stamping, from a relatively compressible sealant material such as RTV. Front piece 44 is next placed over cannula 14 and cup 36 with screw 42 of the latter entering keyway 48, and rotated with cannula 14 as it advances to cause threads 50 to engage threads 52 of housing 24 and compressing O-ring 54 between the proximal end of front piece 44 and housing 24. At the same time, tightening of front piece 44 to housing 24 compresses washer 56 between the internal surface of the distal end of front piece 44 and the outside circular corner of the distal end of cup 36.

The thus assembled probe 10 can be fitted with a suitable fitting, for example, one of fittings 58 and 60, for the supply of irrigation fluid, such as by having an aperture 62 in the side surface of front piece 44, positioned opposite keyway 48 so that upon assembly with cap 36, aperture 62 is in alignment with aperture 40. Preferably aperture 62 is tapped so that either of fitting 58 and 60, fitting 58 preferably being a barbed nipple with a threaded end, and fitting 60 preferably being a Luer fitting, can be threaded into and secured to front piece 44.

In the first preferred embodiment of the invention, as best illustrated in FIGS. 1 and 2, elongated member 12 is hollow and distal end portion 32 of cannula 14 is rounded and partially cut away so that both a portion of its end or tip and its adjacent side surface has been removed forming an aperture 64 in the cannula. In this manner, a portion of the distal end portion 18 of member 12 is exposed.

In the use of the probe of this embodiment, one of the fittings 58 or 60 is mounted in aperture of front piece 44.

Irrigation fluid is supplied (not shown) through the fitting into the interior of front piece 44 and through aperture 40 and through apertures 41 to the interior of cup 36. Irrigation fluid then flows from the interior of cup 36 through the annular space between member 12 and cannula 14 to the interior of distal end portion 32 of the cannula and to the exterior and about the end of distal end portion 18 of elongated member 12. Ultrasonic vibrations transmitted from an ultrasonic motor or transducer (not shown) through horn 26 to member 12, causes the distal end portion 18 of member 12 to vibrate longitudinally, causing the fluid adjacent to end portion 18 and partially confined by cannula 14 to be activated or cavitate. The activated fluid exiting aperture 64 is believed to act upon tissue or other material adjacent the aperture in distal end portion of cannula 14, causing the tissue or material to be fragmented or emulsified. Suction (not shown) is provided to the handpiece 22 and through horn 26 and the interior of elongated member 12. Fluid and fragmented or emulsified tissue and/or material can be removed from the area adjacent aperture 64 by aspiration through aperture 64 regulated by the amount of suction applied to the handpiece 22 and member 12.

In the embodiment thus described, and in the other preferred embodiments of this invention, the amount or depth of tissue and/or other material to be removed can be controlled by the shape and size of the aperture in the distal end portion 32 of cannula 14, such as aperture 64 in the embodiment described above, and the ultrasonic energy power and amplitude and excursion of the elongated member. The surgeon or operator can manipulate the handpiece, and thus direct the distal end portion of the cannula to the precise location of the tissue and/or other material to be removed. The surgeon or operator can also readily remove and replace the cannula with a cannula of another embodiment of this invention during a surgical procedure to select the cannula design most suited for a particular phase of the procedure.

Figure 4:
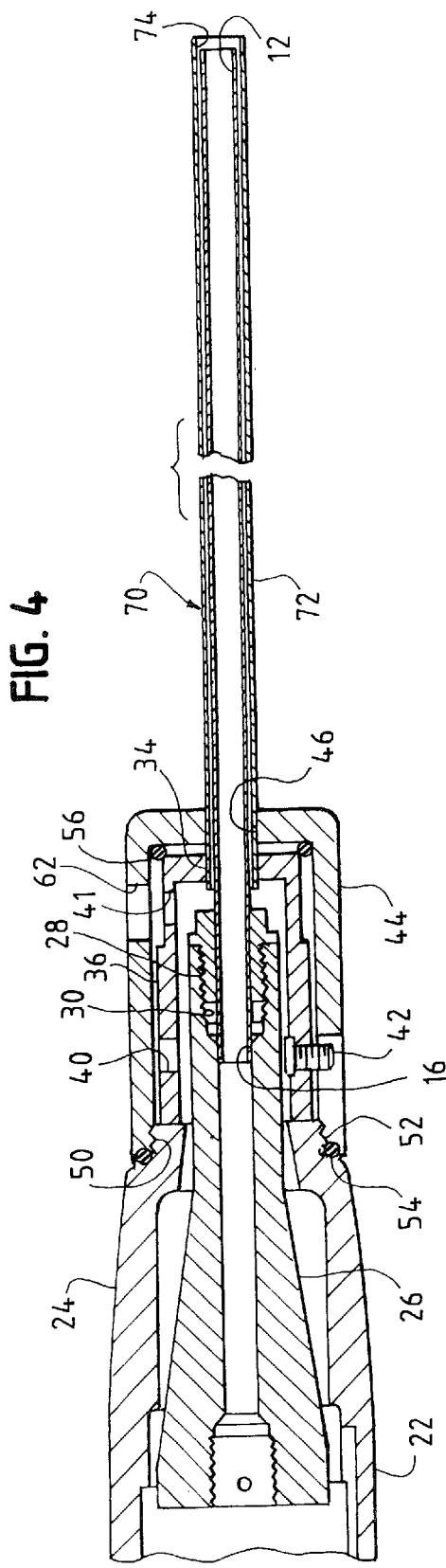
FIG. 4 is a sectional view of the probe illustrated in FIG. 3, assembled and without the fluid supply fittings.

In another embodiment of the invention, as best shown in FIG. 4, wherein like reference numerals refer to substantially similar elements common to the first embodiment, probe 70 has a cannula 72 which is open-ended to form an aperture 74 which includes the entire distal end of the cannula. As in the previous embodiment, cannula 66 extends distally beyond the distal end of member 12, minimizing direct contact of member 12 with tissue of the patient. The assembly and use of probe 70 can be accomplished in the same manner as in the first embodiment, and further explanation is not required.

Another embodiment of the invention is best illustrated in FIG. 5, again with like reference numerals to the first embodiment, wherein probe 80 features a cannula 82 having a relatively elongated aperture 84 having its direction of elongation parallel to the axis on the surface of the cannula spaced from its rounded distal end. The dimensions of the aperture 84 can be selected to control the amount and rate of tissue or other material to be removed from the patient's body. The same manner of assembly and usage as in the previous embodiment can be used for the assembly and use of probe 80.

Still another embodiment is illustrated in FIG. 6, with like reference numbers for elements which are substantially similar to elements of the first embodiment. In this embodiment, probe 90 has a cannula 92 with three apertures 94 spaced equidistantly about the surface of the distal end portion of the cannula and closely spaced to the rounded distal end of the cannula. The manner of use, operation and assembly of probe 90 is substantially similar to the use, operation and assembly of probe 10 in the first embodiment, and further explanation to one skilled in the art is not required.

Optionally, if desired, at least one aperture 95 can be provided in the distal end portion 18 of elongated member 12 to permit pre-aspiration of a portion of the irrigation fluid from the annular space between member 12 and cannula 14 before all of the fluid reaches the distal end of member 12. Pre-aspiration is discussed in earlier patents, such as U.S. Pat. No. 4,493,694.

While particular embodiments of the ultrasonic probe of the invention have been shown and described, it will be appreciated by those skilled in the art that changes and modifications may be made thereto without departing from the invention in its broader aspects and as set forth in the following claims.

What is claimed is:

1. An ultrasonic surgical probe having an ultrasonically isolated, low stress shaped surrounding cannula, comprising:

a. an axially elongated hollow member having a circular cross-section and a proximal end portion adapted to receive ultrasonic vibrations, said member having a distal end which is open-ended and perpendicular to the axis of the member, said member defining a marginal distal end portion thereof adjacent said distal end, said member adapted to receive ultrasonic vibrations at said proximal end and to transmit ultrasonic vibrations from said marginal distal end portion, and adapted to receive and transmit fluid and tissue therethrough; and b. a coaxially positioned cannula surrounding said elongated member, extending beyond the distal end of said member, and isolated from the transmission of ultrasonic vibrations to said member and spaced from said member, said cannula defining a distal end portion, and said distal end portion of said cannula at least partially surrounding the distal end of said member and defining an opening adjacent the distal end of said member.

2. The ultrasonic surgical probe of claim 1, wherein said cannula has a blunt distal end portion.

3. The ultrasonic surgical probe of claim 1, wherein said cannula has a rounded distal end portion.

* * * * *